United States Patent [19]

Clemens et al.

[11] Patent Number: 5,242,956

[45] Date of Patent: Sep. 7, 1993

[54] BONE PHANTOM MATERIAL WITH HIGH HOMOGENEITY

[75] Inventors: Anton H. Clemens, Madison; Kenneth F. Erfourth, Mt. Horeb, both of Wis.

[73] Assignee: Radiation Measurements, Inc., Madison, Wis.

[21] Appl. No.: 849,906

[22] Filed: Mar. 12, 1992

[51] Int. Cl.$^5$ .............................. A61K 6/08; C08J 9/32
[52] U.S. Cl. ................................. 523/117; 523/113; 523/218; 523/219; 264/328.17; 264/328.18
[58] Field of Search ............... 523/117, 113, 218, 219; 524/417, 430; 264/328.18, 328.17

[56] References Cited

U.S. PATENT DOCUMENTS

| | | | |
|---|---|---|---|
| 4,439,386 | 3/1984 | Antczak | 264/328.18 |
| 4,451,584 | 5/1984 | Schaefer | 523/113 |
| 5,019,605 | 5/1991 | Jannic | 523/219 |

OTHER PUBLICATIONS

White, D. R. and R. J. Martin, "Epoxy Resin Based Tissue Substitutes," 50 *British Journal of Radiology* 814–821 (1977).

*Primary Examiner*—Paul R. Michl
*Assistant Examiner*—LaVonda DeWitt
*Attorney, Agent, or Firm*—Quarles & Brady

[57] ABSTRACT

A method of producing highly homogeneous material, for constructing bone density phantoms used in calibrating CT machines and the like, dehumidifies the x-ray absorbing constituents of the material and combines them under vacuum to reduce the effects of absorbed atmospheric moisture and of air entrained by the mixing process. The binding polymer into which the x-ray absorbing materials are added is predoped with hardener to increase its viscosity to a point that prevents the migration of the components during the hardening process but that does not prevent their adequate dispersion throughout the mixture. Molds are filled by transferring the unhardened material through a tube connected to the bottom of the mixing vessel and to the bottom of the mold to further prevent the entrainment of air.

10 Claims, 3 Drawing Sheets

BONE PHANTOM MATERIAL WITH HIGH HOMOGENEITY

BACKGROUND OF THE INVENTION

This invention relates generally to X-ray phantoms for calibrating CT machines and the like, and specifically to a method of manufacturing an X-ray phantom for simulating bones of various mineral content.

X-rays passing through materials, such as those of the human body, are attenuated. Materials such as bone produce greater attenuation than muscle or other connective tissue and this difference in attenuation can be used to produce an image of these internal body structures, for example, on an X-ray sensitive film exposed by the X-rays passing through the body.

Differences in attenuation, as well as distinguishing between soft tissue and bone, may be used to distinguish between similar tissues of different densities. For example, bone of greater density provides greater attenuation than bone of lesser density. Information on bone density is valuable in the detection and treatment of disease involving bone degeneration, such as osteoporosis.

Conventional radiographic images, as described above, produce a "shadow picture" of internal body structures, the exposure or relative "brightness" at each point in the image representing the total attenuation of all tissue along a line between the X-ray source and that point on the film. As a result, the quantitative measurement of bone density is complicated by the presence of attenuating tissue on either side of the bone.

This problem of isolating the attenuation effect of an internal element of the body, such as a bone, from the surrounding tissue has been largely eliminated with the advent of computerized tomographic imaging systems (CT systems). CT systems use multiple X-ray exposures and a computer "reconstruction" process to generate tomographic or slice images of the human body. The slice images show relative X-ray attenuation, independently, for a variety of volume elements ("voxels") along the cross section of the image. The attenuation is represented by a CT number derived from the reconstruction process and used to define the brightness of the slice image at that point. The CT number for voxels within the bones of the body, as selected with reference to the slice image, thus provides an indication of bone density at those voxels unaffected by surrounding tissue. The advent of CT machines has therefore provided a convenient method of measuring bone density in vitro.

In measuring bone density with a CT system, a region of interest "ROI" is defined, by reference to the CT slice image, around a portion of bone to be measured. Frequently the trabecular bone of the spine is selected for this measurement. The average of the CT numbers of a number of voxels associated with that ROI provide a direct measure of bone density. This value of bone density may be compared to similarly derived values for the same patient at different times.

Unfortunately, the CT numbers produced by a given CT machine scanning a particular object, vary over time. A given object will also produce different CT numbers when scanned by different CT machines. These variations result primarily from changes or differences in the characteristics of the X-ray tubes used to produce the X-rays, primarily energy or spectral characteristics, and from variations in the sensitivity of the detectors which receive and measure the attenuated X-rays.

For this reason, it is typical to calibrate the CT machine used to evaluate bone density with a "phantom" material of accurate and known density placed in proximity to the patient. The calibration is performed by "normalizing" the CT numbers of the image with the CT number of voxels within the phantom.

Ideally, the material of the phantom perfectly mirrors the qualities of the tissue being studied. For example, when bone density is being evaluated, the phantom should have attenuation qualities identical to that of bone. Of particular concern is that the spectral characteristics of the attenuation, the amount of attenuation of the X-rays as a function of X-ray energy or frequency, closely match the tissue being studied. This spectral matching is important because the energy of the X-ray beam between CT machines may vary widely.

Studies have indicated that there are primarily two physical mechanisms accounting for X-ray attenuation: "photoelectric absorption" and "Compton scattering". It follows from this fact that any material may be synthesized by the appropriate combination of two basis materials having relatively different photoelectric absorption and Compton scattering, and by adjusting the total density of the mixture thus produced without changing the ratio of this mixture. For bone, the two basis materials of choice are calcium and aluminum compounds.

A known recipe for making a bone mineral phantom requires mixing of calcium and aluminum compounds into a flexible plastic resin. The ratio between the calcium and aluminum controls the spectral characteristics of the material. Fine, air-filled microspheres are added to the mixture to adjust the total density of the composition.

In practice, the manufacture of bone mineral phantoms according to this recipe is difficult. The primary problem results from the high degree of homogeneity required of the phantom. Ideally, the phantom material must exhibit a homogeneity within three CT numbers, each which represents one-tenth of one percent variation in attenuation. Further this homogeneity must be not only throughout the volume of the phantom but also between different phantoms, i.e., between each batch of the phantom material. An individual voxel measured in the CT image may be only a few millimeters square, and thus this high degree of homogeneity must exist on an extremely small scale.

Each of the ingredients used in constructing the phantom material can be precisely measured, and the use of microspheres containing air allows accurate control of the amount of air introduced for controlling density. Nevertheless, the required degree of homogeneity has been nearly impossible to achieve, especially between separate batches of the material. Of course, batch to batch homogeneity can be achieved, by measuring and selecting the material according to its particular attenuation qualities, however, this is expensive and time consuming.

SUMMARY OF THE INVENTION

The present invention provides a method of compounding and molding bone mineral phantom material to provide a high degree of homogeneity. In particular, the present invention identifies the causes of variations of homogeneity in the phantom material; particularly that of entrained air, humidity and the natural separation of the various ingredients which have different densities. Problems, such as the uneven loss of materials to the mixing surfaces and damage of the microspheres, are also identified and addressed by the method of this invention.

Specifically, it is one object of the invention to reduce the separation of the ingredients of a bone mineral phantom by accurately controlling the viscosity of the binder polymer at the time of mixing. By "predoping" the polymer, the viscosity of the mixture is adjusted to make the precise trade-off between preventing separation of the ingredients during hardening and interfering with the even dispersion of the ingredients throughout the mixture.

It is another object of the invention to eliminate variations in density caused by air unintentionally trapped during the mixing process and to provide flexibility in selecting the viscosity of the mixture, without increasing or affecting the amount of air unintentionally trapped within the mixture. This object is accomplished by mixing the phantom material in a vacuum.

It is a further object of the invention to provide a means for transferring the mixed phantom material to a mold without trapping air. The compounded phantom material is transferred through the bottom of the mixing container through a tube to the bottom of a mold. This transfer method and the bottom filling of the mold prevents the entrainment of air.

Other objects and advantages besides those discussed will be apparent to those skilled in the art from the description of the preferred embodiment of the invention which follows. In the description, reference is made to the accompanying drawings which form a part hereof, and which illustrate one example of the invention. Such example, however, is not exhaustive of the various alternative forms of the invention, and therefore reference is made to the claims which follow the description for determining the full scope of the invention.

DESCRIPTION OF THE PREFERRED EMBODIMENT INGREDIENTS

Figure 1:
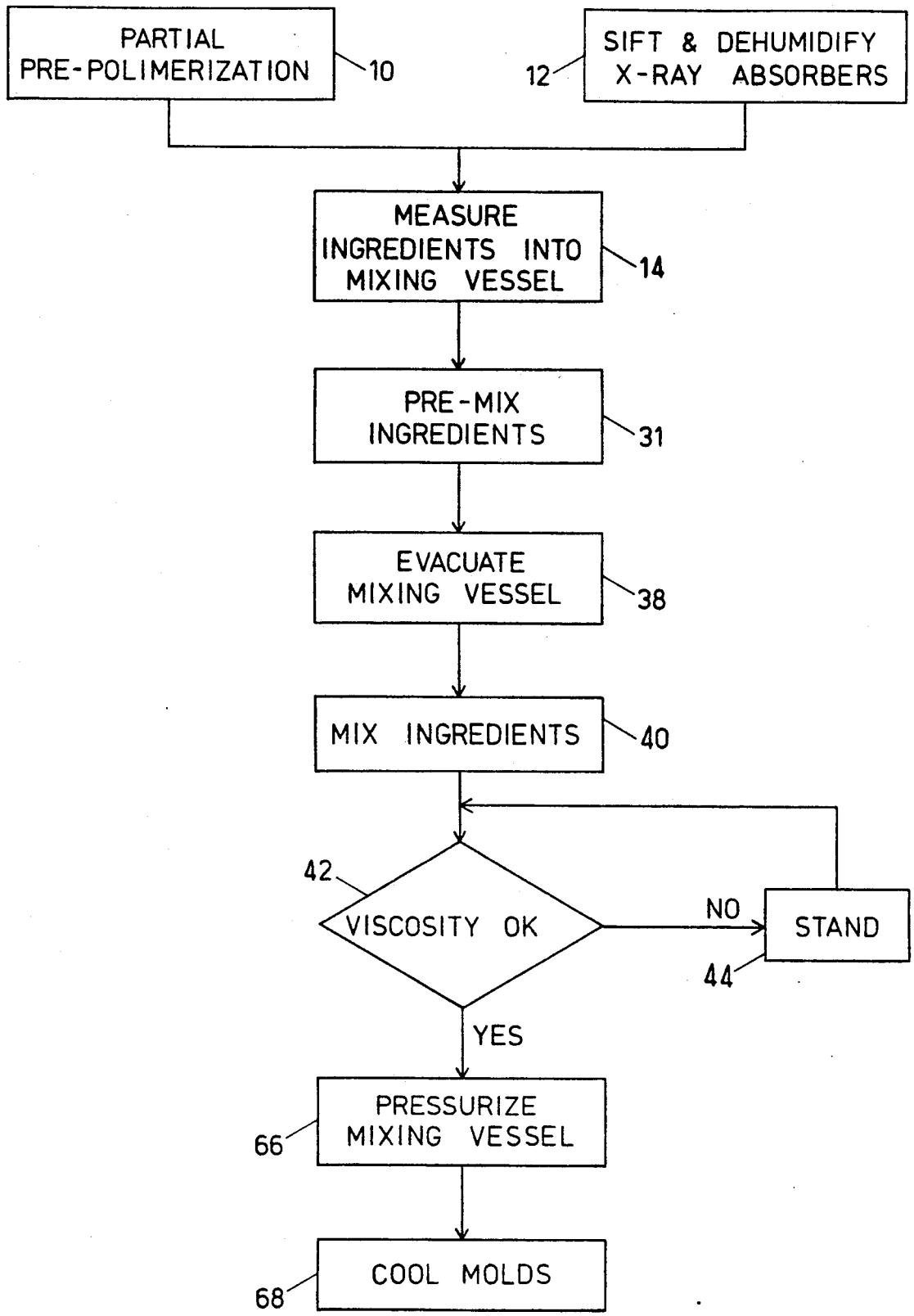
FIG. 1 is a flowchart showing the steps of the method of the present invention.

As shown in Table I, phantom material as produced by the method of the present invention is comprised of four principle constituents: (1) a polymer binder (in turn comprised of a resin and hardener or catalyst), (2) a stabilizer, (3) one or more X-ray absorbing materials and (4) a density control material.

As the name suggests, the polymer binder serves primarily to hold together the other constituents of the mixture and to provide the bulk and flexibility necessarily for convenient handling. The stabilizer is a particulate material whose presence hampers the migration of the other materials to prevent them from settling out. The X-ray absorbing materials are the materials that primarily provide the desired X-ray attenuation for the phantom material. It should be understood that all of the materials in the phantom material attenuate X-rays to some degree and that the designation "x-ray absorbing materials" is merely intended to denote the materials primarily responsible for the X-ray attenuation characteristics of the result mix. The density control material is phenolic microspheres which contain air so as to have an attenuation of less than any of the other materials. The phenolic microspheres thus provide a convenient way of adjusting the total attenuation of the bone mineral material, without affecting the ratio among the X-ray absorbing materials, and, thus, the spectral characteristics of the phantom material.

TABLE I

| PHANTOM TYPE CT # | Type | RESIN Epon | HARDENER TMD | STABILIZER P.E. | X-RAY ABSORBING MATERIAL | | | DENSITY CONTROL MATERIAL PMS |
|---|---|---|---|---|---|---|---|---|
| | | | | | Ca. Phos. | AlO$_3$ | Fumed AlO$_3$ | |
| 0 | Water | 58% | 5% | 22% | 0% | 9% | 3% | 2% |
| 75 | Bone | 54% | 5% | 21% | 7% | 9% | 2.5% | 2% |
| 100 | Bone | 52% | 5% | 20% | 9% | 9% | 2.25% | 2% |
| 150 | Bone | 50% | 5% | 19% | 14% | 9% | 1% | 2% |

The choice of binder and stabilizer agents are largely immaterial to the X-ray absorption characteristics of the phantom material. Nevertheless, they affect the ease with which the materials may be combined and ultimate mechanical property of the material formed. In a preferred embodiment, the resin is a dimer fatty acid-based epoxy resin such as Epon Resin 871, manufactured by the Shell Oil Co. One preferred hardener is a 2,2,4 trimethylenehexamethylene Diamine, such as Vestamin TMD, sold by HULS AG. of Piscataway, N.J.

The stabilizer may be a powdered polyethylene having a powder size of approximately 20 microns such as Polyethylene F microfine powder sold by Quantum Chemical Corp. of Cincinnati, Ohio.

In the preferred embodiment, the X-ray absorbing materials are of two types, calcium materials and aluminum materials. In the preferred embodiment, the calcium material is calcium phosphate tribasic such as is manufactured by Monsanto Chemicals under the name of Tricalcium Orthophosphate 3Ca(PO4)$_2$.Ca(OH)$_2$ 3H$_2$0. The aluminum compounds are of two different types, the first being levigated alumina (AlO$_3$) and the second being the fumed alumina, which is chemically identical to the levigated alumina but has a flake form which decreases the mobility of the alumina within the mixture, thus serving to reduce the separation of the components. It will be recognized from this description to those of skill in the art that other materials having divergent Compton scattering and photoelectric effect absorption may be used in place of the X-ray absorbing materials described here. The relative quantities of such adjusted materials will, of course, have to be adjusted according to their particular absorption characteristics.

The phenolic microspheres are UCAR thermoset microballoons sold by Union Carbide Chemicals and Plastics Company of Danbury, Conn. It will be understood that other materials having similar properties may be substituted for those described above as will be generally understood to those of ordinary skill in the art.

Referring again to Table I, four phantom materials may be produced, differing from each other in the CT number of their attenuation: a first material with a CT number of 0, simulating water (by definition) and three subsequent materials with higher CT numbers simulating various densities of bone. The difference between these materials arises from the amount of calcium phosphate and alumina used; the other materials change, only in percentage as necessitated by their displacement by these X-ray absorbing materials. The hardener and PMS appear to remain constant because their minor variation is absorbed in rounding the percentage figures.

COMPOUNDING

The present invention has identified a number of sources of variation or heterogeneity. One principal factor, causing heterogeneity within a single batch of phantom material, is clumping and separation of the various constituent ingredients. In the prior art, this separation was reduced by the addition of the stabilizing material and by the selection of forms of the X-ray absorbing materials that resist migration within the resin.

In the present invention these methods of reducing separation are augmented by adjusting the viscosity of the resin at the time of mixing. The viscosity of the resin is increased sufficiently to prevent migration of the materials through the resin once it is molded, but not so much as to prevent homogeneous mixing.

Referring then to FIG. 1, the first step in compounding the phantom material is performing a "partial prepolymerization" of the resin, performed by predoping the resin with a portion of its hardener to increase its viscosity, as shown in process block 10. The amount of the hardener used will depend on the particular resin, the temperature of the resin and the time prior to its being used. The proper amount of hardener is determined for a particular situation to adjust the viscosity of the resin mixture to be approximately 7000 mPas at the time of the mixing. In the present embodiment, approximately 20% of the total hardener ultimately needed for the given quantity of resin is added to the resin at this stage. The hardener is mixed with the resin; at this point the viscosity of the mixture is sufficiently low so that entrained air is not a problem. The mixed hardener and resin is allowed to stand at room temperature overnight.

As shown by process block 12, the X-ray absorbers are sifted and dehumidified. This process 12 may be performed as shown, or after process block 10, to usefully employ the time during the partial preliminary polymerization.

The dehumidification of process block 12 is performed first under partial vacuum, to allow the removal of excess water from the X-ray absorbers without heating, the latter which would cause the calcium phosphate to clump, to the detriment of its mixing. The dehumidification accomplishes three goals. First, the dehumidified X-ray absorbers sift better and, therefore, mix without clumping. Second, removal of the water permits higher vacuum levels to be obtained during the mixing, to be described, which contributes to better homogeneity in the product. Three, the dehumidification removes the water from the mixture which may affect the total X-ray absorptivity and thus cause the batch-to-batch homogeneity to vary, depending upon the atmospheric humidity during the mixing.

After dehumidification by vacuum, the alumina and calcium phosphate tribasic are sifted through 250 micron screens and placed in smaller containers. A typical batch will employ about 850 grams of alumina and varying amounts of calcium phosphate tribasic as shown in Table I. The fumed alumina is not sifted.

As shown by process block 14, the resin and the sifted and dehumidified X-ray absorbing materials are measured into a mixing vessel for mixing. The mixing vessel is placed on a scale and the scale zeroed to provide confirmation of the amount of materials actually added to the mixing vessel during the measuring process. This is particularly important in the case of the resin which is sufficiently viscous so that a significant portion of the resin will not be transferred to the mixing vessel but will remain adhered to the inner walls of the measuring container. Approximately 5 kg. of resin and 500 grams of hardener are transferred to the mixing container in a typical batch.

The resin is transferred first to prevent the dry materials from caking at the bottom of the mixing vessel. Next, the remaining hardener is added and three drops (less than a 1/10 of a gram) of an antifoaming agent are also added. The antifoaming agent may be a combination of polydimethylsiloxane and silica such as in Antifoam A compound sold by Dow Corning Chemical Corp. of Midland, Mich. After sufficient resin and hardener have been added, the polyethylene is added and then the dehumidified X-ray absorbing materials are added in this order: calcium phosphate, fumed alumina, PMS and levigated alumina. The order is important because calcium phosphate and fumed alumina develop static electricity and will otherwise fly out of the container in significant quantities during the mixing procedure. The PMS and levigated alumina act as a "cap" to contain these powders. All of the ingredients are added at this stage of process block 14.

Figure 2:
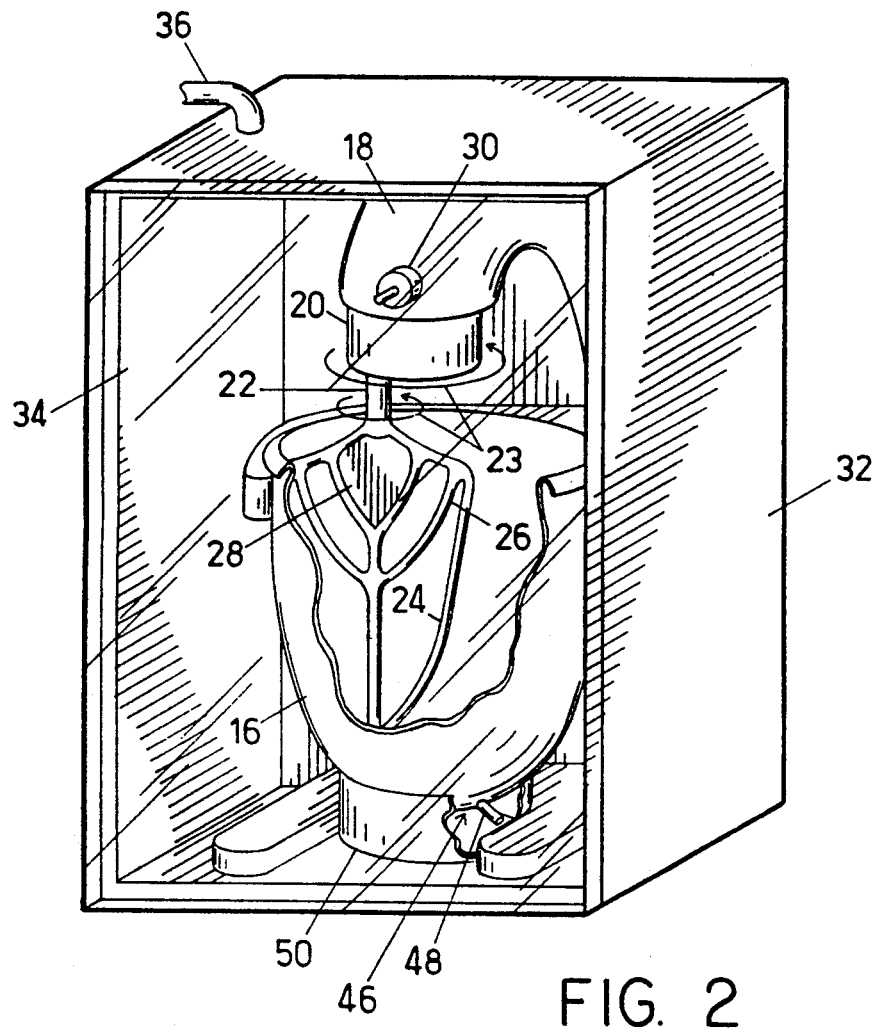
FIG. 2 is a perspective view of a mixing vessel and mixing unit contained in a vacuum chamber, as used in the mixing step shown of FIG. 1.

As shown in FIG. 2, the mixing vessel 16 may be a stainless steel bowl for fitting into a commercial mixing unit 18 such as are common in large commercial or institutional kitchens. The mixing unit 18 employs a gear head 20 providing a hypocycloidic rotation of a shaft 22 connected to a shield shaped stirring paddle 24. The stirring paddle 24 includes a set of branching veins 26 for stirring the mixture contained within the bowl 16 and is modified so that a center cavity 28, formed by the veins 26 near the shaft 22, is filled with epoxy to prevent unmixed materials from becoming lodged in this cavity 28.

The hypocycloidic rotation of the paddle 24 provides a constant scraping of the paddle 24 against the interior of the mixing vessel 16 to prevent unmixed materials from aggregating in this area. An accessory shaft 30 connected by gearing to shaft 22 provides a means of manually rotating the paddle 24 by a crank (not shown) engaging accessory shaft 30.

After the materials have first been introduced into the mixing vessel 16, the paddle 24 is turned by hand slowly until all the powders (the X-ray absorber, the stabilizer and the PMS) are wetted by the liquid resin and hardener. This prevents the powders from flying out of the mixing bowl once the motor of the mixing unit 18 is turned on. When the powders are wetted, the mixing unit 18 is started at slow speed. The slow speed breaks up large clumps of the dry powders and mixes the ingredients together. This prevents clumps of any particular ingredient from sticking to the top of the bowl and not mixing in which could throw off the ratio of ingredients needed for the phantom materials. Referring to FIG. 1, this premixing step is indicated by process block 31.

Once the premixing step 31 is complete, the mixing vessel 18 is stopped and the mixing unit is changed to the next highest mixing speed.

Referring again to FIG. 2, the mixing vessel 16 and mixing unit 18 are contained within a vacuum chamber 32 having a clear Plexiglass front panel 34. The mixer unit 18 is then started and the front panel 34 is closed and sealed and the air is evacuated from the vacuum chamber 32, through exhaust pipe 36. A vacuum of approximately 5,000 mTorr is achieved within approximately four minutes as indicated by process block 38 in FIG. 1. The ingredients are mixed together by the mixing unit 18, as indicated by process block 40, a stage which requires approximately one hour. The evacuation of the chamber 32 prevents the entrainment of air into the mix, such air entrainment being uncontrollable and having an unpredictable effect on the total attenuation qualities of the phantom material, particularly between batches.

After one hour, as indicated by decision block 42, the mixing unit 18 is stopped and the vacuum released. Material from the mixing bowl 16 is evaluated for viscosity. The desired viscosity is 10,000-12,000 mPas although it will be understood that variations in this viscosity may be acceptable depending upon the particular materials used. Ideally, the viscosity is such as to permit adequate mixing of the materials yet to resist migration of the PMS and X-ray absorbing materials within the resin during hardening, which may create homogeneity problems after the materials have been introduced into a mold. If, at decision block 42, the viscosity is not adequate, the materials are allowed to stand for 15 minutes without mixing, as shown by process block 44, and the viscosity is checked again at decision block 42. This "loop" of decision block 42 and process block 44 is repeated until the mixture reaches the proper viscosity.

Figure 3:
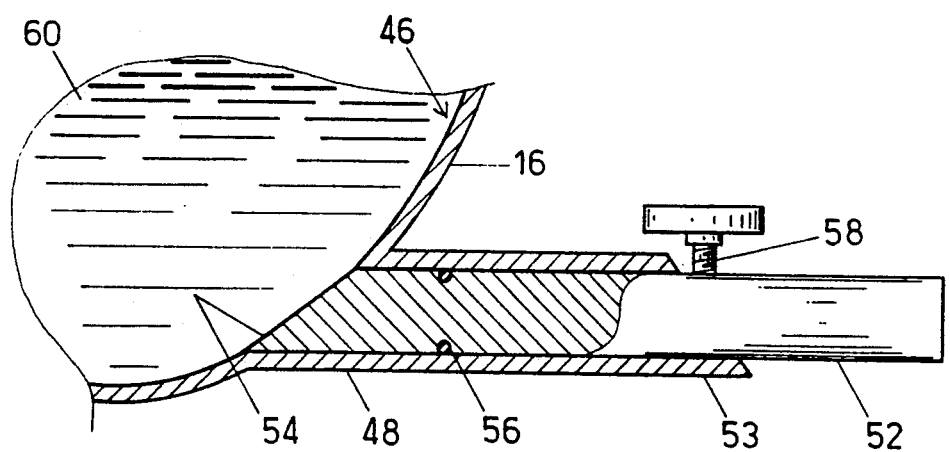
FIG. 3 is a detail in cross section of the mixing vessel of FIG. 2 in cross section showing an orifice and plug at the bottom of the mixing vessel, as used to transfer the phantom material to a mold.

Referring now to FIG. 3, the mixing vessel 16 has been modified by the introduction of an orifice 46 connected to short tube 48 extending out from the bottom of the vessel 16. During the mixing process of blocks 31 and 40, the tube 48 is protected by a support ring 50 fitting over the bottom of the vessel 16 and around that portion holding the tube 48 to prevent the vessel 16 from resting on the tube 48.

During the measuring and mixing of the ingredients of process blocks 14-44, the tube 48 is blocked by a cylindrical plug 52 fitting within the tube 48 and having a first end 54 contoured to match the inner surface of the mixing vessel 16 at orifice 46. An 0-ring 56 contained within a circumferential notch near the first end 54 provides positive sealing between the plug 52 and the inner surface of the tube 48. Finally, a threaded screw 58 extending diametrically through the plug 52 to strike and affect lip 53 at the outer end of the tube 48, may be tightened so as to prevent movement of the plug 52 in and out of the tube 48.

Figure 4:
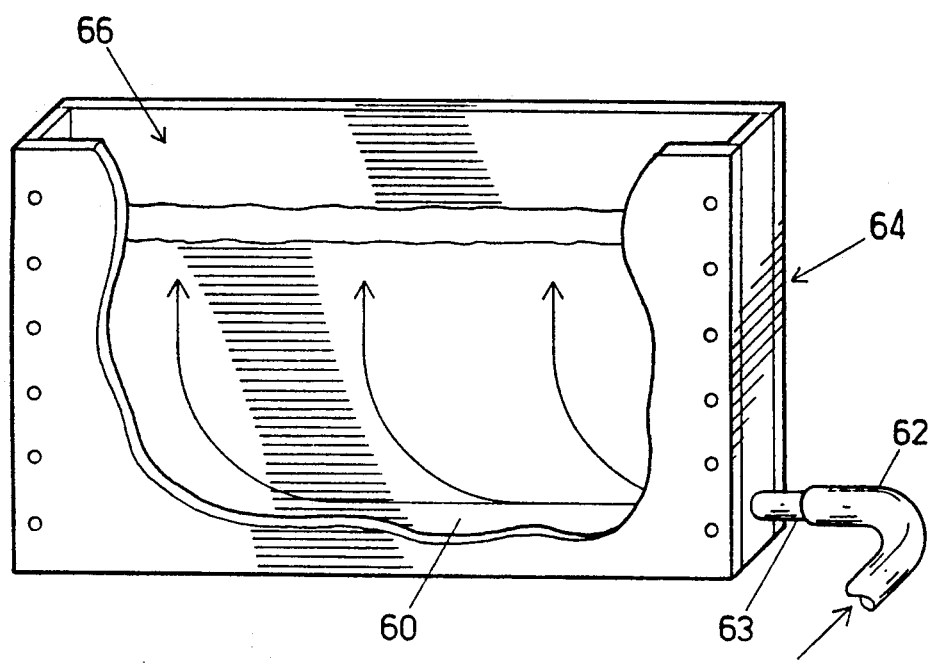
FIG. 4 is a fragmentary perspective view of a mold showing the path of the phantom material as received from the mixing vessel and orifice of FIG. 3.

When the mixing and viscosity of the phantom material is satisfactory, per process blocks 40 and 42 of FIG. 1, the plug 52 is removed from the tube 48 to permit the passage of phantom material 60 through the orifice 46 and the tube 48. Referring to FIG. 4, a flexible hose 62 having one end attached to a mold 64 has its other end slipped over the surface of the tube 48 to receive phantom material 60 from the vessel 16 and to transmit that material through the hose 62 and a tube 63 communicating with the bottom of the mold 64. The mold 64 forms a generally regular parallelepiped interior volume 66 for receiving the mold material 60 and holding the mold material 60 until it has cured to solid form.

The viscosity of the phantom material 60 is such that this flow does not occur spontaneously.

Hence, the phantom material 60 is forced through the tube 48 and the flexible hose 62 to the mold 64 by the application of air pressure to the mold material 60 contained within the mixing vessel 16 by an airtight lid (not shown) fitted to the top of the mixing vessel 16. The air pressure required to move the phantom material 60 from the bowl 16 to the mold 64 is 5 to 20 PSI.

It will be understood that this transfer of phantom material 60 from the mixing vessel 16 to the mold 64 also reduces possible entrainment of air in the phantom material 60 by filling the mold cavity 66 from the bottom upward. This should be contrasted with filling of the mold cavity 66 from the top down where air could be trapped under the descending phantom material 60. Referring once again to FIG. 1, this step of transferring the phantom material 60 to the mold 64 is represented by process block 66.

Once the transfer of phantom material 60 is complete, the hose 62 is removed from the mold 64 and a plug similar to the plug 52 used with tube 48 is used to plug the inlet tube 63 of the mold 64 to prevent phantom material 60 from leaking out of the mold volume 66.

Per process block 68 shown in FIG. 1, the mold is then placed in circulating air to provide cooling for the solidification of the phantom 60. The required air pressure to move the phantom material 60 from the bowl 16 to the mold 64 is 5 to 20 PSI. Once the phantom material 60 has set, the molds are cured in a heating bin for three days at 67° C.

EXAMPLE

Ingredients as listed in the amounts given in Table II were combined to produce a phantom material simulating water. The fumed alumina and levigated alumina were evacuated at a vacuum of 600 mTorr and then combined with the Epon, TMD, antifoam polyethylene and PMS. After premixing a vacuum of less than 1 Torr was applied and the ingredients mixed at 85 RPM for 60 minutes. At the end of this time, the viscosity was 5350 mPas at 31°C. Mixing was resumed for 10 minutes with the viscosity reaching 13,000 mPas at 29° C. The mixture was allowed to stand for 35 minutes at which time the viscosity was 7,000 mPas at 34° C. The molds were then filled by pressurizing the mixed container as described above.

The materials for the phantoms were allowed to set. The phantoms were removed and scanned in a CT instrument and the variation in CT numbers were totaled. The variation in CT numbers within the slab were between four and five which equates to a percentage variation of approximately 0.4%-0.5%.

TABLE II

| | INGREDIENTS | MASS | PERCENTAGE |
|---|---|---|---|
| 1. | Epon | 5203.8 g | 57.82% |

TABLE II-continued

| | INGREDIENTS | MASS | PERCENTAGE |
|---|---|---|---|
| 2. | TMD | 484.2 g | 5.38% |
| 3. | Antifoam | 0.5 g | 0.01% |
| 4. | Polyethylene | 1847.7 g | 20.53% |
| 5. | Fumed Alumina | 270.0 g | 3.00% |
| 6. | Calcium Tribasic | 0.0 g | 0.0% |
| 7. | PMS | 238.5 g | 2.65% |
| 8. | Lev. Alumina | 955.8 g | 10.62% |
| | TOTALS | 9000.5 g | 100.01% |

I claim:

1. A method of manufacturing an x-ray phantom material formed of a mixture of a predetermined amount of a polymer binder, an x-ray attenuating material and air filled microspheres, the polymer binder including both a resin and a corresponding measure of a hardener, the method comprising the steps of:
   combining the resin and a portion of the corresponding measure of the hardener;
   allowing the combined resin and hardener to stand to reach a predetermined viscosity.
   dehumidifying the x-ray attenuating materials under partial vacuum;
   combining the dehumidified x-ray attenuating material, the combined resin and hardener, the balance of the corresponding portion of the hardener, and the air filled microspheres in a mixing vessel; and
   stirring the combined ingredients in the mixing vessel under vacuum.

2. The method as recited in claim 1 wherein the full amount of the dehumidified x-ray attenuating material and the polymer binder and the air filled microspheres are combined together prior to the stirring of the combined ingredients under vacuum.

3. The method as recited in claim 1 wherein the mixing vessel has a sealable bottom orifice and including the steps of:
   connecting the bottom orifice to the bottom interior of a mold;
   unsealing the bottom orifice; and
   raising the interior pressure of the mixing vessel to force the combined and stirred ingredients out of the mixing vessel into the mold.

4. A method of manufacturing an x-ray phantom material formed of a mixture of a predetermined amount of a polymer binder, an x-ray attenuating material and air filled microspheres, the polymer binder comprising a resin and a corresponding measure of hardener, the method comprising the steps of:
   combining the resin and a portion of the corresponding measure of the hardener;
   allowing the combined resin and hardener to stand to reach a predetermined viscosity;
   combining the x-ray attenuating material, the remaining measure of hardener and the air filled microspheres in a mixing vessel; and
   stirring the combined ingredients in the mixing vessel under vacuum.

5. The method as recited in claim 4 wherein the full amount of the x-ray attenuating material and the polymer binder and air filled microspheres are combined together prior to the stirring of the combined ingredients under vacuum.

6. The method as recited in claim 4 wherein the x-ray attenuating material is dehumidified under a vacuum prior to combining with the other ingredients.

7. The method as recited in claim 4 wherein the mixing vessel has a sealable bottom orifice and including the steps of:
   connecting the bottom orifice to the bottom interior of a mold;
   unsealing the bottom orifice; and
   raising the interior pressure of the mixing vessel to force the combined and stirred ingredients out of the mixing vessel into the mold.

8. A method of manufacturing an x-ray phantom material formed of a polymer binder, an x-ray attenuating material and air filled microspheres, the polymer binder comprising both a resin and a corresponding measure of a hardener, the method comprising the steps of:
   combining the resin and a portion of the corresponding measure of the hardener;
   allowing the combined resin and hardener to stand to reach a predetermined viscosity;
   combining the x-ray attentuating material, the combined resin and hardener, the balance of the corresponding measure of the hardener, and the air filled microspheres in a mixing vessel; and
   stirring the combined ingredients in the mixing vessel under vacuum, the mixing vessel having a sealable bottom orifice;
   unsealing the bottom orifice; and
   raising the interior pressure of the mixing vessel to force the combined and stirred ingredients out of the mixing vessel into a mold.

9. The method as recited in claim 8 wherein the full amount of the x-ray attenuating material and the polymer binder and air filled microspheres are combined together prior to the stirring of the combined ingredients under vacuum.

10. The method as recited in claim 8 wherein the x-ray attenuating material is dehumidified under a vacuum prior to combining with the other ingredients.

* * * * *